United States Patent [19]

Driscoll

[11] Patent Number: 4,614,871

[45] Date of Patent: Sep. 30, 1986

[54] PHOTODIODE

[76] Inventor: John N. Driscoll, 25 Geraldine Dr., Wellesley Hills, Mass. 02181

[21] Appl. No.: 666,990

[22] Filed: Oct. 31, 1984

[51] Int. Cl.[4] .................... H01J 40/16; G01N 21/33
[52] U.S. Cl. ................................ 250/372; 250/373; 313/539; 313/542
[58] Field of Search ............... 313/539, 542, 544; 250/372, 211 R, 213 R, 213 VT, 373

[56] References Cited

U.S. PATENT DOCUMENTS

| | | | |
|---|---|---|---|
| 1,917,854 | 7/1933 | Rentschler | 313/539 |
| 3,638,059 | 1/1972 | Taylor | 313/539 |
| 3,771,005 | 11/1973 | Erickson | 313/539 |

OTHER PUBLICATIONS

Sampson, J. A. R., "Vacuum Ultraviolet", Wiley, 1965, pp. 224–245.
Canfield, L. R., Johnston, R. G., and Madden, R. P., "NBS Detector Standards for the Far Ultraviolet", *Applied Optics*, Jul. 1973, vol. 12, No. 7, pp. 1611–1617.
Driscoll, J. N. and Ferioli, P., "Detector for GC Works in Far UV", *Research & Development*, Sep. 1984, pp. 104–107.

*Primary Examiner*—Carolyn E. Fields

[57] ABSTRACT

A non-evacuated photodiode for detecting far-uv radiation. The photocathode is a cylindrical element surrounded by an annular anode. The photocathode is constructed of a metal (e.g., nickel) that emits electrons only in response to far-uv radiation of 140 nanometer or shorter wavelengths. A window (e.g., magnesium fluoride) is positioned at the entrance to the photodiode, to filter out far-uv radiation with wavelengths shorter than about 100 nanometers. The window and photocathode material serve to make the photodiode sensitive to radiation in a wavelength range to greater than 100 to 140 nanometers. A high-temperature perfluoroethylene material is used as an insulating layer for spacing the window from the anode and for spacing the anode from the photocathode. The photodiode is used in a gas chromatography detector.

13 Claims, 3 Drawing Figures

PHOTODIODE

BACKGROUND OF THE INVENTION

This invention relates to photodiodes for detecting far-uv radiation.

Far-uv radiation (wavelengths of less than 200 nanometers) has conventionally been detected using evacuated photodiodes. Examples of evacuated photodiodes are disclosed in Canfield et al., "NBS Detector Standards for the Far Ultraviolet", Applied Optics, vol. 12, pp. 1611-17 (July 1973). In one such vacuum photodiode (FIG. 2 of Canfield et al.), the ultraviolet radiation enters an evacuated chamber through a magnesium fluoride window, passes through the center of an anode ring surrounding the window, crosses the evacuated chamber, and strikes a photocathode (rubidium telluride or cesium telluride). The electrons emitted by the photocathode pass back across the evacuated chamber to the anode ring, creating a current that is measured externally. Canfield et al. also discloses windowless photodiodes, but these, too, are operated in a vacuum. A text on detectors authored by Sampson and published by Wiley in about 1965 discusses (section 7.3, pp. 224-244) photoelectron emmission generally, and describes evacuated photodiodes.

SUMMARY OF THE INVENTION

I have discovered that an effective far-uv photodiode can be constructed without evacuating the interior of the device. In preferred embodiments, far-uv radiation entering the photodiode travels no more than 10 mm before reaching the photocathode (which is a sufficiently short distance to keep oxygen absorption of the radiation to no more than about 80-90%); the photocathode is a cylindrical element surrounded by an annular anode; the photocathode is constructed of a metal (e.g., nickel) that emits electrons only in response to far-uv radiation of 140 nanometer or shorter wavelengths (i.e., whose photoelectric yield is 5% or less above 140 nanometers); a window (e.g., magnesium fluoride) is positioned at the entrance to the photodiode, to filter out far-uv radiation with wavelengths shorter than about 100 nanometers (i.e., the intensity of radiation of shorter wavelengths is attenuated by at least 90% in passing through the window); the window and photocathode material serve to make the photodiode sensitive to radiation in a wavelength range no greater than 100 to 140 nanometers; a high-temperature perfluoroethylene material is used as an insulating layer for spacing the window from the anode and for spacing the anode from the photocathode.

The new photodiode has many advantages. It is more reliable and rugged. It exhibits less background noise and dark current, largely because it is preferably not sensitive to radiation above 140 nanometers. It is relatively inexpensive to manufacture, in part because the complex and expensive manufacturing processes associated with producing an evacuated device have been eliminated, and in part because the photocathode itself is less expensive and simpler to manufacture.

In a second aspect, the invention features a gas chromatography ("GC") detector sensitive only to radiation with wavelengths in the range of 100 to 140 nanometers (i.e., its sensitivity to radiation outside that range is less than 10% of its maximum sensitivity within the range). We have discovered that making the detector sensitive to such a wavelength range gives it wider application because all gases (except noble gases) absorb radiation in that wavelength range. A further advantage is that the response factors for organic compounds such as methanol or benzene are similar (e.g., within a factor of four) within the 100 to 140 nanometer range. In preferred embodiments, the detector has a far-uv lamp emitting radiation principally in the 100 to 140 nanometer range and a non-evacuated photodiode sensitive to radiation in the same range.

Other features and advantages of the invention will be apparent from the following description of a preferred embodiment.

DESCRIPTION OF THE PREFERRED EMBODIMENT

Figure 1:
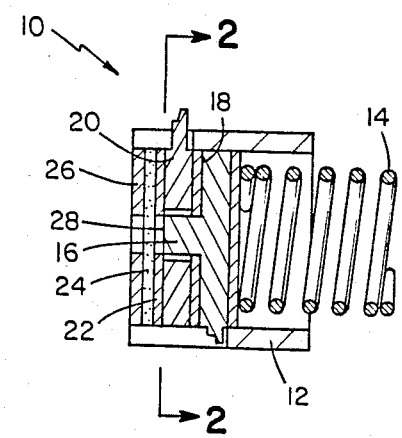
FIG. 1 is a cross sectional view of the preferred photodiode of the invention.
Figure 2:
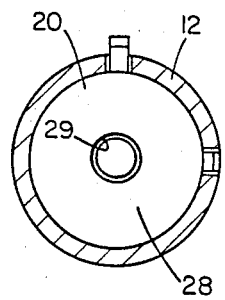
FIG. 2 is a cross sectional view at 2—2 of FIG. 1.

Referring to FIGS. 1 and 2, there is shown a far-uv photodiode 10 consisting of a cylindrical housing 12 containing (working from the bottom up) compression spring 14, photocathode 16 (nickel), insulator 18 (Dupont Kalrez, a perfluoroethylene derivative), anode 20 (nickel), second insulator 22 (Kalrez), window 24 (magnesium fluoride), and third insulator 26 (Kalrez). The active surface 28 of photocathode 16 is positioned 1 to 2 mm beneath window 24, meaning that far-uv radiation entering the photodiode need only travel 1 to 2 mm before striking the photocathode. The active surface is the upper surface of a cylindrical projection of the photocathode that fits inside a slightly larger opening 29 in the annular anode 20. The radial spacing between the cathode and anode is only a few thousandths of an inch, enough to allow an adequate field strength to be created between the two electrodes without any shorting.

Figure 3:
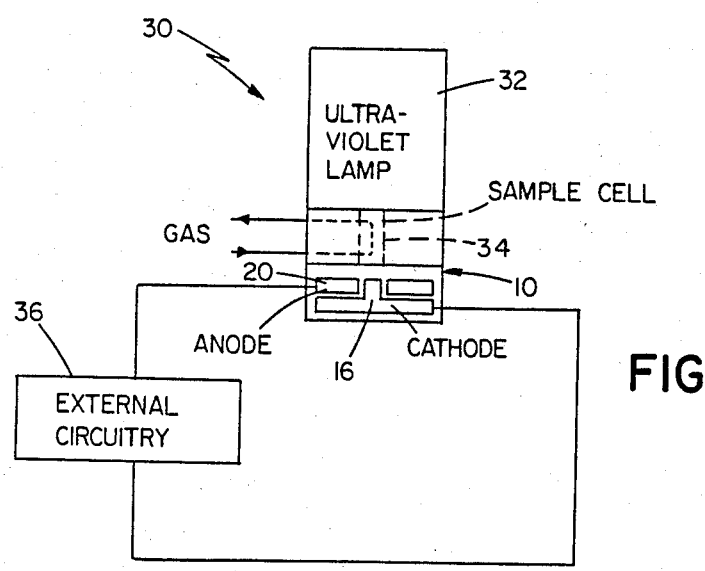
FIG. 3 is a diagrammatic view of the preferred gas chromatography detector of the invention.

Referring to FIG. 3, there is shown a GC detector 30 having an ultraviolet lamp 32 emitting radiation in a narrow range around 120 nanometers. Radiation from the lamp passes through sample cell 34, which receives gases leaving a gas chromatography column. Radiation not absorbed by the gases strikes photodiode 10, which generates a current (detected by external circuitry 36) proportional to the intensity of incident radiation in the 110 to 130 nanometers wavelength range. An electric potential is placed across the two electrodes 16, 20 by external circuitry 36 to provide the electric field between the electrodes.

The narrow wavelength range of the photodiode is due to the combined effects of window 24 and photocathode 16. Window 24 passes only radiation with wavelengths greater than 110 nanometers (i.e., radiation below that wavelength is attenuated by at least 90% in passing through the window). Photocathode 16 is sensitive only to radiation with wavelengths less than 130 nanometers (i.e., its photoelectric yield above 130 nanometers is less than 5%).

The Kalrez material used between the window and the anode or between the anode and cathode has the beneficial property of becoming sticky at the high temperatures (about 300 degrees Celsius) at which the GC detector operates. This stickiness permits the Kalrez to act as a seal against gases in chamber 34 entering photodiode 10 and prevents relative movement of the anode and cathode.

I hereby incorporate by reference the disclosure of Driscoll et al., "Detector for GC works in Far UV", Research & Development, pp. 104-7, September 1984.

Other embodiments are within the following claims. For example, other metals could be used for the electrodes and windows such as lithium fluoride and sapphire could be used.

I claim:

1. A photodiode device for far-uv radiation comprising:

a radiation entry zone;

a photocathode positioned at one end of said zone in the path of far-uv radiation entering from the other end and passing through said zone; and an anode positioned to collect electrons emitted by said photocathode; characterized in that:

said radiation entry zone is neither evacuated nor filled with inert gas;

the distance between said other end of said entry zone and said photocathode is sufficiently short that absorption of said radiation within said zone is no greater than 90% in the presence of oxygen-containing atmospheric gases; and the spacing between said photocathode and said anode is sufficiently small to allow the creation of field strength adequate for operation of said photodiode device with atmospheric gases filling said spacing.

2. The photodiode device of claim 1 further comprising a window at the other end of said radiation entry zone.

3. The photodiode device of claim 2 wherein said radiation path is less than 10 mm in length.

4. The photodiode device of claim 2 wherein said window is made of magnesium fluoride.

5. The photodiode device of claim 2 wherein said window filters out far-uv radiation with wavelengths shorter than 100 nanometers.

6. The photodiode device of claim 2 further comprising a high-temperature perfluoroethylene material as an insulating layer spacing said window from said anode or said anode from said photocathode.

7. The photodiode device of claim 1 wherein said photocathode is a cylindrical element and said anode is an annular element surrounding said photocathode.

8. The photodiode device of claim 7 wherein the spacing between said anode and photocathode is annular and a few thousandths of an inch in width.

9. A photodiode device of claim 1 wherein said photocathode is constructed of a metal that emits electrons predominantly in response to far-uv radiation of 140 nanometers or shorter wavelengths.

10. The photodiode device of claim 9 wherein said metal is nickel.

11. The photodiode device of claim 1 wherein said window and photocathode device material serve to make said photodiode sensitive predominantly to radiation in a wavelength range no greater than 100 to 140 nanometers.

12. The photodiode device of claim 1 wherein said distance between the other end of said entry zone and said photocathode is from 1-2 mm.

13. A gas chromatography detector comprising a source of far-uv radiation in the 100 to 140 nanometer wavelength range, a sample cell through which gases flow and said radiation passes, a photodiode device sufficient for detecting the far-uv radiation emerging from said cell, and means for positioning said photodiode device so that radiation emerging from said cell passes through said photodiode device, said photodiode device comprising a radiation entry zone;

a photocathode positioned at one end of said zone in the path of far-uv radiation entering from the other end and passing through said zone; and an anode positioned to collect electrons emitted by said photocathode; characterized in that:

said radiation entry zone is neither evacuated nor filled with inert gas;

the distance between said other end of said entry zone and said photocathode is sufficiently short that absorption of said radiation within said zone is no greater than 90% in the presence of oxygen-containing atmospheric gases; and the spacing between said photocathode and said anode is sufficiently small to allow the creation of field strength adequate for operation of said photodiode device with atmospheric gases filling said spacing.

* * * * *